United States Patent
Everett et al.

(10) Patent No.: US 10,769,418 B2
(45) Date of Patent: Sep. 8, 2020

(54) DEVICES AND SYSTEMS FOR COLLECTIVE IMPACT ON MENTAL STATES OF MULTIPLE USERS

(71) Applicant: AT&T Intellectual Property I, L.P., Atlanta, GA (US)

(72) Inventors: Sarah P. Everett, Cedar Park, TX (US); Greg W. Edwards, Austin, TX (US); Marc Andrew Sullivan, Austin, TX (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 660 days.

(21) Appl. No.: 15/411,540

(22) Filed: Jan. 20, 2017

(65) Prior Publication Data
US 2018/0206725 A1 Jul. 26, 2018

(51) Int. Cl.
*G06K 9/00* (2006.01)
*A61B 5/11* (2006.01)
*A61B 5/00* (2006.01)
*A61B 5/16* (2006.01)

(52) U.S. Cl.
CPC ........ *G06K 9/00302* (2013.01); *A61B 5/1116* (2013.01); *A61B 5/165* (2013.01); *A61B 5/4884* (2013.01); *G06K 9/00885* (2013.01); *G06K 2009/00939* (2013.01)

(58) Field of Classification Search
None
See application file for complete search history.

(56) References Cited

U.S. PATENT DOCUMENTS

| 6,731,307 | B1 | 5/2004 | Strubbe et al. |
| 7,378,955 | B2 | 5/2008 | Mazar et al. |
| 7,665,024 | B1 | 2/2010 | Kondziela |
| 8,390,439 | B2 | 3/2013 | Cruz-Hernandez |
| 8,787,332 | B2 | 7/2014 | Ha et al. |
| 9,046,884 | B2 | 6/2015 | Roseway et al. |

(Continued)

FOREIGN PATENT DOCUMENTS

| EP | 2 515 760 | 10/2012 |
| EP | 30 062 198 | 8/2016 |

(Continued)

OTHER PUBLICATIONS

Klein, Jonathan, Youngme Moon, and Rosalind W. Picard. "This computer responds to user frustration:: Theory, design, and results." Interacting with computers 14.2 (2002): 119-140. https://pdfs.semanticscholarorg/b675/42398227d8583a7c96663e687de93910e655.pdf.

(Continued)

*Primary Examiner* — James B Hull

(57) ABSTRACT

Devices, computer-readable media and methods for affecting mental states of a first user and a second user are disclosed. For example, a processor may receive first biometric data for a first user, quantify a mental state of the first user based upon the first biometric data, receive second biometric data for a second user, and quantify a mental state of the second user based upon the second biometric data. The processor may further select a first automated action to affect the mental state of the first user and the mental state of the second user, and implement the first automated action to affect the mental state of the first user and the mental state of the second user.

19 Claims, 3 Drawing Sheets

(56) References Cited

U.S. PATENT DOCUMENTS

| | | |
|---|---|---|
| 9,047,871 B2 | 6/2015 | Dimitriadis et al. |
| 9,098,109 B2 | 8/2015 | Lappalainen et al. |
| 9,149,236 B2 | 10/2015 | Chun et al. |
| 9,223,935 B2 | 12/2015 | Heneghan et al. |
| 9,399,111 B1 | 7/2016 | Hanina |
| 9,418,390 B2 | 8/2016 | Chun et al. |
| 2007/0050150 A1 | 3/2007 | Levy et al. |
| 2007/0167689 A1 | 7/2007 | Ramadas et al. |
| 2009/0002178 A1 | 1/2009 | Guday et al. |
| 2011/0263946 A1 | 10/2011 | El Kaliouby et al. |
| 2013/0245396 A1 | 9/2013 | Berman et al. |
| 2013/0297536 A1 | 11/2013 | Almosni et al. |
| 2014/0287387 A1 | 9/2014 | Vukasinovic et al. |
| 2015/0339363 A1* | 11/2015 | Moldoveanu .......... G16H 50/20 707/723 |

FOREIGN PATENT DOCUMENTS

| | | |
|---|---|---|
| WO | WO 02075688 | 9/2002 |
| WO | WO 2007/019584 | 2/2007 |
| WO | WO 2015/033152 | 3/2015 |
| WO | WO 2015/067534 | 5/2015 |
| WO | WO 2016/127157 | 8/2016 |
| WO | WO 2016/130232 | 8/2016 |
| WO | WO 2016/142351 | 9/2016 |

OTHER PUBLICATIONS

Picard, Rosalind W., and Jonathan Klein. "Computers that recognise and respond to user emotion: theoretical and practical implications." Interacting with computers 14.2 (2002): 141-169. http://courses.media.mit.edu/2004spring/mas630/Articles/PK-IWC.pdf.

LiKamWa, Robert, et al. "Can your smartphone infer your mood." PhoneSense workshop. 2011. http://niclane.org/pubs/likamwa_phonesense.pdf.

Picard, Rosalind W. "Toward computers that recognize and respond to user emotion." IBM systems journal 39.3.4 (2000): 705-719.

Picard, Rosalind W. "Toward computers that recognize and respond to user emotion." IBM systems journal 39.3.4 (2000): 705-719.

* cited by examiner

DEVICES AND SYSTEMS FOR COLLECTIVE IMPACT ON MENTAL STATES OF MULTIPLE USERS

The present disclosure relates to the use of biometric sensors and other network-connected devices to quantify users' mental states, and to the implementation of automated actions to affect the users' mental states in a predetermined manner via various network-connected devices.

BRIEF DESCRIPTION OF THE DRAWINGS

The teaching of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
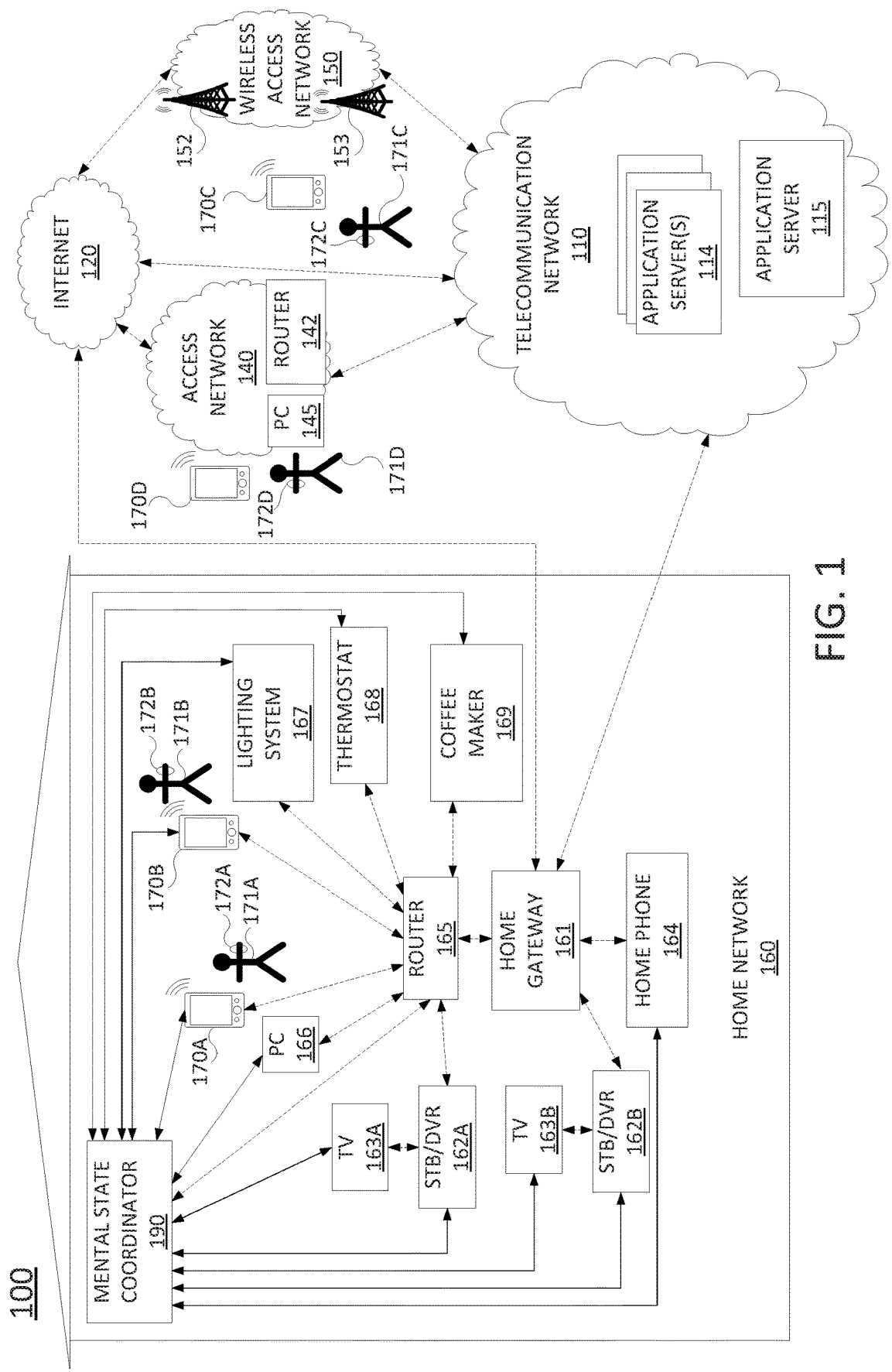
FIG. 1 illustrates an example network or system related to the present disclosure.

Devices, computer-readable media and methods for affecting mental states of a first user and a second user are disclosed. For example, a processor may receive first biometric data for a first user, quantify a mental state of the first user based upon the first biometric data, receive second biometric data for a second user, and quantify a mental state of the second user based upon the second biometric data. The processor may further select a first automated action to affect the mental state of the first user and the mental state of the second user, and implement the first automated action to affect the mental state of the first user and the mental state of the second user.

In one example, the mental state of first user is quantified into a first mental state score based upon the first biometric data, and the mental state of second user is quantified into a second mental state score based upon the second biometric data. The first automated action may be selected to affect the mental state of the first user and the mental state of the second user in a first predetermined manner, e.g., to increase at least one of the first mental state score or the second mental state score, to decrease at least one of the first mental state score or the second mental state score, or to maintain at least one of the first mental state score or the second mental state score. In one example, the first automated action is selected to affect the mental state of the first user and the mental state of the second user in a first predetermined manner based upon a priority ranking between the first user and the second user. For instance, the priority ranking may be based upon a relationship between the first user and the second user, such as: a parent-child relationship, a caregiver-charge relationship, a vendor-client relationship, etc. In one example, the first automated action is selected to have a greater anticipated effect on the first mental state score as compared to the second mental state score, in accordance with the first predetermined manner.

In one example, the first automated action is implemented at a location where the first user and the second user are anticipated to be co-located. In one example, the first automated action is implemented on at least one of: an appliance at the location, a television at the location, a stereo at the location, a mobile device of the first user, or a mobile device of the second user. The first automated action may comprise, for example: adjusting a temperature of an environment associated with the first user and the second user; presenting an audio program, a video program, an image, or a document for the first user and the second user; adjusting a lighting of the environment associated with the first user and the second user; preparing beverages for the first user and the second user; and so forth.

In one example, the first automated action is selected from among a plurality of available automated actions in accordance with an effectiveness score of the first automated action for the first user and an effectiveness score of the first automated action for the second user. In one example, each of the plurality of available automated actions is assigned an effectiveness score for the first user and an effectiveness score for the second user. For instance, an effectiveness score for an automated action with respect to a user may be based upon quantifications of a mental state of the user both before and after one or more historical implementations of the automated action with respect to the user.

In one example, after the implementation of the first automated action to affect the mental state of the first user and the mental state of the second user, the processor may further determine whether the mental state of the first user and the mental state of the second user were affected in the first predetermined manner. When the processor determines that the mental state of the first user and the mental state of the second user were not affected in the first predetermined manner, the processor may decrease an effectiveness score of the first automated action for the first user and/or decrease and effectiveness score of the first automated action for the second user. In addition, the processor may select a second automated action to affect the mental state of the first user and the mental state of the second user in a second predetermined manner, and implement the second automated action to affect the mental state of the first user and the mental state of the second user in the second predetermined manner. These and other aspects of the present disclosure are discussed in greater detail below in connection with the examples of FIGS. 1-3.

To aid in understanding the present disclosure, FIG. 1 illustrates an example system 100, related to the present disclosure. As shown in FIG. 1, the system 100 connects mobile devices 170A-170D, personal computer (PC) 145, and home network devices such as home gateway 161, set-top boxes (STBs) 162A, and 162B, television (TV) 163A and TV 163B, home phone 164, router 165, personal computer (PC) 166, lighting system 167, thermostat 168, coffee maker 169, and so forth, with one another and with various other devices via a telecommunication network 110, a wireless access network 150 (e.g., a cellular network), an access network 140, and Internet 120.

In one embodiment, each of mobile devices 170A-170D may comprise any subscriber/customer endpoint device configured for wireless communication such as a laptop computer, a Wi-Fi device, a Personal Digital Assistant (PDA), a mobile phone, a smartphone, an email device, a computing tablet, a messaging device, and the like. In one embodiment, any one or more of mobile devices 170A-170D may have both cellular and non-cellular access capabilities and may further have wired communication and networking capabilities. In one example, mobile devices 170A-170D may be used by users 171A-171D, who may be associated with one another as family members, e.g., parents and children, as friends, as co-workers, as caregiver and charge(s), and so forth. In one example, each of the users 171A-171D may further have at least one respective biometric sensor 172A-172D, e.g., a wearable device, that may be in communication with one of the mobile devices 170A-170D, e.g., via a wired or a wireless connection, such as a via an infrared transmitter or transceiver, a transceiver for IEEE 802.11 based communications (e.g., "Wi-Fi"), IEEE 802.15 based communications (e.g., "Bluetooth", "ZigBee", etc.), and so forth. Alternatively, or in addition, any one or more of biometric sensors 172A-172D may connect to various networks independently of a respective mobile device. The biometric sensors 172A-172D may include: heart rate monitors, electrocardiogram devices, acoustic sensors, sensors for measuring users' breathing rates, galvanic skin response (GSR) devices, portable electroencephalography (EEG) devices, event-related potential (ERP) measurement devices, diffuse optical tomography (DOT) scanners, and so forth.

In one example, the biometric sensors 172A-172D may measure or capture data regarding various physical parameters of a user (broadly, "biometric data") from which a mental state, e.g., a mood or emotional state, may be calculated. For instance, the biometric sensors 172A-172D may record users' heart rates, breathing rates, skin conductance and/or sweat/skin moisture levels, temperature, blood pressure, voice pitch and tone, body movements, e.g., eye movements, hand movements, and so forth. In another example, the biometric sensors 172A-172D may measure postures of users 171A-171D. For instance, a slouching posture may be associated with depression or sadness, while sitting or standing straight is more correlated with happiness or contentment. In another example, the biometric sensors 172A-172D may measure brain activity, e.g., electrical activity, optical activity, chemical activity, etc., depending upon the type of biometric sensor.

As illustrated in FIG. 1, users 171A-171D appear to have one biometric sensor apiece. However, it should be understood that users 171A-171D may each have any number of different biometric sensors. In one example, data gathered by biometric sensors 172A-172D may be used to calculate or determine the users' mental states. In addition, relevant biometric data for users 171A-171D may also be gathered from other devices, such as PC 145, PC 166, TV 163A, TV 163B, mobile devices 170A-170D, and so forth, as described in greater detail below. For example, the TVs 163A may have an attached or integrated camera for obtaining facial image data of a viewer, and/or an attached or integrated microphone for recording voice(s) within recording range of the microphone. PC 145, PC 166, TV 163B, and mobile devices 170A-170D may be similarly equipped. Thus, in one example, PC 166, PC 145, TV 163A, TV 163B, or one of mobile devices 170A-170D may capture video or still images of users' faces. Similarly, PC 166, PC 145, TV 163A, TV 163B, or one of mobile devices 170A-170D may record audio data of users' voices from which pitch, tone, and other parameters may be calculated. Alternatively, or in addition, words and phrases in the audio data may also be determined, e.g., using speech recognition techniques. In another example, a keyboard of PC 166 or PC 145 may record forces of keystrokes, mobile devices 170A-170D may record forces of presses on touchscreens of the respective devices, and so forth.

In one example, telecommunication network 110 may combine core network components of a cellular network with components of a triple play service network; where triple-play services include telephone services, Internet services, and television services to subscribers. For example, telecommunication network 110 may functionally comprise a fixed mobile convergence (FMC) network, e.g., an IP Multimedia Subsystem (IMS) network. In addition, telecommunication network 110 may functionally comprise a telephony network, e.g., an Internet Protocol/Multi-Protocol Label Switching (IP/MPLS) backbone network utilizing Session Initiation Protocol (SIP) for circuit-switched and Voice over Internet Protocol (VoIP) telephony services. Telecommunication network 110 may also further comprise a broadcast television network, e.g., a traditional cable provider network or an Internet Protocol Television (IPTV) network, as well as an Internet Service Provider (ISP) network. For example, with respect to television service provider functions, application servers 114 may represent one or more television servers for the delivery of television content, e.g., a broadcast server, a cable head-end, and so forth. For instance, telecommunication network 110 may comprise a video super hub office, a video hub office and/or a service office/central office. With respect to cellular core network functions, application servers 114 may represent a Home Subscriber Server/Home Location Register (HSS/HLR) for tracking cellular subscriber device location and other functions, a serving gateway (SGW), a packet data network gateway (PGW or PDN GW), a mobility management entity (MME), and so forth. Application servers 114 may further represent an IMS media server (MS) for handling and terminating media streams to provide services such as announcements, bridges, and Interactive Voice Response (IVR) messages for VoIP and cellular service applications.

As shown in FIG. 1, telecommunication network 110 may also include an application server 115. In one example, the application server 115 may comprise a computing system, such as computing system 300 depicted in FIG. 3, and may be configured to provide one or more functions for affecting mental states of a first user and a second user, in accordance with the present disclosure. For example, application server 115 may be configured to perform one or more steps, functions, or operations in connection with the example method 200 described below. It should be noted that as used herein, the terms "program," "configure," and "reconfigure" may refer to programming or loading a computing device with computer-readable/computer-executable instructions, code, and/or programs, e.g., in a memory, which when executed by a processor of the computing device, may cause the computing device to perform various functions. Such terms may also encompass providing variables, data values, tables, objects, or other data structures or the like which may cause a computer device executing computer-readable instructions, code, and/or programs to function differently depending upon the values of the variables or other data structures that are provided. For ease of illustration, various additional elements of telecommunication network 110 are omitted from FIG. 1.

In one embodiment, wireless access network 150 comprises a radio access network implementing such technologies as: global system for mobile communication (GSM), e.g., a base station subsystem (BSS), or IS-95, a universal mobile telecommunications system (UMTS) network employing wideband code division multiple access (WCDMA), or a CDMA3000 network, among others. In other words, wireless access network 150 may comprise an access network in accordance with any "second generation" (2G), "third generation" (3G), "fourth generation" (4G), Long Term Evolution (LTE) or any other yet to be developed future wireless/cellular network technology. While the present disclosure is not limited to any particular type of wireless access network, in the illustrative embodiment, wireless access network 150 is shown as a UMTS terrestrial radio access network (UTRAN) subsystem. Thus, base stations 152 and 153 may each comprise a Node B or evolved Node B (eNodeB). As illustrated in FIG. 1, mobile device 170C may be in communication with one or both of base stations 152 and 153, which provide connectivity between mobile device 170C and other endpoint devices within the system 100, various network-based devices, such as application servers 114, and so forth. In addition, in one example biometric sensor 172C may also be in communication with one or both of base stations 152 and 153, e.g., where biometric sensor 172C is also equipped for cellular communication. In one example, wireless access network 150 may be operated by the same or a different service provider that is operating telecommunication network 110.

In one example, access network 140 may comprise a Digital Subscriber Line (DSL) network, a broadband cable access network, a Local Area Network (LAN), an enterprise network, or the like. In one example, access network 140 may include a router 142 for wired and/or wireless communication with endpoint devices, such as PC 145, mobile device 170D, biometric device/wearable device 172D, and so forth. For ease of illustration, various other components of access network 140 are omitted from FIG. 1, such as a gateway, firewall devices, additional PCs, printers, faxes, storage devices, and so forth. In one example, access network 140 may transmit and receive communications between personal computer (PC) 145, and other devices in the system 100 relating to voice telephone calls, communications with web servers via the Internet 120, telecommunication network 110, and/or wireless access network 150, and so forth.

In one example, home network 160 may include a home gateway 161, which receives data/communications associated with different types of media, e.g., television, phone, and Internet, and separates these communications for the appropriate devices. In one example, television data is forwarded to set-top boxes (STBs)/digital video recorders (DVRs) 162A and 162B to be decoded, recorded, and/or forwarded to television (TV) 163A and TV 163B for presentation. Similarly, telephone data is sent to and received from home phone 164; Internet communications are sent to and received from router 165, which may be capable of both wired and/or wireless communication. In turn, router 165 receives data from and sends data to the appropriate devices, e.g., personal computer (PC) 166, mobile devices 170A, and 170B, lighting system 167, thermostat 168, coffee maker 169, and so forth. In one example, router 165 may further communicate with TV (broadly a display) 163A and/or 163B, e.g., where one or both of the televisions is a smart TV. In one example, router 165 may comprise a wired Ethernet router and/or an Institute for Electrical and Electronics Engineers (IEEE) 802.11 (Wi-Fi) router, and may communicate with respective devices in home network 160 via wired and/or wireless connections. In this regard, it should be noted that lighting system 167, thermostat 168, and coffee maker 169 may comprise "smart" appliances, with wired and/or wireless networking/communication capability. Thus, such appliances may be remotely programmed or configured, and may communicate operational data to remote devices via one or more networks or network links. Similarly, TVs 163A and 163B, STBs/DVRs 162A and 162B, and/or home phone 164 may also comprise smart appliances with wired and/or wireless networking/communication capability, which may be remotely programmed or configured, and which may communicate operational data to remote devices via one or more networks or network links. For instance, each of these devices may include a transceiver for IEEE 802.11-based communications, for IEEE 802.15-based communications, for wired communications, e.g., for wired Ethernet, and so forth.

In one example, home network 160 may also include a mental state coordinator 190. In one example, the mental state coordinator 190 may comprise a computing system, such as computing system 300 depicted in FIG. 3, and may be configured to provide one or more functions for affecting mental states of a first user and a second user, in accordance with the present disclosure. For example, mental state coordinator 190 may be configured to perform one or more steps, functions, or operations in connection with the example method 200 described below. As illustrated in FIG. 1, mental state coordinator 190 may be in communication with various devices/appliances within home network 160. In this regard, mental state coordinator 190 may also include a transceiver for IEEE 802.11-based communications, for IEEE 802.15-based communications, for wired communications, e.g., for wired Ethernet, and so forth.

As mentioned above, users 171A-171D may be associated with one another in various ways. For illustrative purpose, in one example, users 171A-171D may comprise family members. In addition, the family members (users 171A-171D) may be associated with home network 160 and may have granted permission to mental state coordinator 190 to gather biometric data regarding the respective users 171A-171D, to use the biometric data to determine the user(s) mental states, and to select and implement automated actions with respect to various devices/appliances within home network 160 in order to affect the users' mental states in a predetermined manner. In one example, the mental state coordinator 190 may utilize biometric data regarding two or more of the users 171A-171D in order to quantify the mental states of the two or more of the users 171A-171D, and to determine and implement an automated action to collectively affect the mental states of the two or more of the users 171A-171D. It should be noted that as described herein, functions of mental state coordinator 190 may similarly be performed by application server 115 in telecommunication network 110. However, for illustrative purposes, examples are described primarily in connection with mental state coordinator 190.

In one example, the mental state coordinator 190 may gather biometric data from mobile devices 170A-170D and/or biometric sensors 172A-172D via home network 160, access network 140, wireless access network 150, Internet 120, telecommunication network 110, etc. In one example, the mental state coordinator 190 may also gather biometric data from devices/appliances within the home network 160. For instance, PC 166, TV 162A, and/or TV 1626 may include a camera which may capture video and/or images of users' faces, gestures, etc. PC 166, TV 162A, and/or TV 162B may further include a microphone which may capture audio of users' voices, including tone, pitch, specific words and phrases that are spoken, and so forth. Similarly, PC 145 in access network 140 may further include a camera and/or a microphone for capturing biometric data of user 171D. For example, PC 145 may comprise a computer at a work/office location of the user 171D.

In one example, the mental state coordinator 190 may gather biometric data for each of the users 170A-170D, and may quantify a respective mental state for each of the users 170A-170D based upon the biometric data. In one example, mental states may include positive mental states such as, happy, excited, relaxed, content, calm, cheerful, optimistic, pleased, blissful, amused, refreshed, or satisfied; negative mental states such as sad, angry, upset, devastated, mad, hurt, sulking, depressed, annoyed, or enraged; and neutral mental states such as indifferent, bored, sleepy, and so on. These mental states are only examples and are not to be interpreted as limitations of the present disclosure. In one example, different mental states may have different signatures or profiles to which biometric data that is gathered from various biometric sensors, e.g., biometric sensors 172A-172D, or to which data derived from the biometric data may be compared in order to determine a most likely current mental state for each of the respective users 171A-171D. The signatures may be based upon various types of biometric data, e.g., depending upon the types of the biometric sensors 172A-172D that are in use and the types of biometric data that the biometric sensors 172A-172D collect, depending upon the types of additional devices that collect biometric data, e.g., PC 145, PC 166, etc., the nature of the biometric data that such devices gather, and so forth.

For example, if the biometric data for user 171A includes facial image data gathered from mobile device 170A, the mental state coordinator 190 may calculate the mental state of user 171A, at least in part, using pattern matching, e.g., to eigenfaces of user 171A based upon a training data set, or composite eigenfaces representative of various mental states/moods over a training data set from faces of various users and for different mental states/moods. In another example, mental state coordinator 190 may calculate a mental state of user 171D from audio data gather via biometric sensors 172D, mobile device 170D, PC 145, and/or other devices in system 100. For instance, the audio data may be compared to various signatures or profiles for different mental states, and a best matching mental state may be calculated as the current mental state for the user 171D. In one example, the calculating may include comparing the words and/or phrases recorded to various profiles or signatures for different moods, e.g., where the profiles/signatures may comprise dictionaries or word lists that include words and/or phrases that are representative of the respective moods.

In still another example, biometric data gathered by mental state coordinator 190 from biometric sensor 172C for user 171C may include heart rate and/or breathing data. Thus, in one example, the mental state of the user 171C may be determined based, at least in part, upon the heart rate or breathing rate data. For instance, an elevated heart rate or breathing rate, e.g., as compared to a baseline/resting rate for the user 171C, may be indicative of duress, fear, etc. It should be noted that different types of biometric data may be aggregated and matched to signatures/patterns for different moods that are comprised of multiple data points that account for the different types of biometric data. Alternatively, or in addition, one or more types of biometric data may be used to match a pattern/signature for a mental state, while one or more other types of biometric data available for the user may be used to verify the accuracy of the mental state that is determined for the user. For instance, if it is determined that the user 171A is in a "fearful" mental state based upon facial image data, while the heart rate and/or breathing rate of user 171A is below a threshold rate, mental state coordinator 190 may determine that the user 171A is not actually in fear since it would normally be expected that the heart rate and breathing rate of user 171A would be elevated if the user 171A were in a "fearful" mental state. For example, the user 171A may be making a face acting as if in fear, without actually being in fear.

In one example, mental state coordinator 190 may categorize a user as being in an overall positive mental state, an overall negative mental state, or an overall neutral mental state (e.g., a quantification scale having three values of −1, 0, and +1), based upon the mental state that may be determined from profile/signature matching. For instance, if it is determined that the user 171B is "dejected," the user 171B may be noted to be in an overall negative mental state. If it is determined that the user 171B is "excited," the user 171B may be noted to be in an overall positive mental state. Other examples of positive, negative, and neutral mental states are mentioned above. It should be noted that in other examples, various other gradations of mental states may be utilized. For instance, five categories of mental states may be deployed (e.g., quantified as states 1-5, states 0-4, states −2 to +2, etc.). For instance, the categories may comprise: very negative, somewhat negative, neutral, somewhat positive, and very positive. Thus, in one example, various mental states may be assigned to one of the five different categories. If a user's mental state is determined, e.g., via signature/pattern matching, the mental state may then be quantified based upon whichever one of the five categories the mental state is assigned.

In one example, a user's mental state/mood may be categorized along one or more scales or dimensions, e.g., a Profile of Mood States (POMS), or the like. For instance, a mental profile of a user may comprise ratings or scores in several broad categories of mood/emotion such as, anger-hostility, confusion-bewilderment, etc., along a five point scale, a ten point scale, etc. In one example, a user's mental state may be broadly classified as being a positive mental state or a negative mental state by determining the mental state/mood within a two or three dimensional space, e.g., according to an evaluative space model, a circumplex model, a vector model, a Positive Activation-Negative Activation (PANA) model, or the like. In one example, a user's mental state/mood that is quantified along one or more scales or dimensions, e.g., in accordance with POMS, PANA, a circumplex model, a vector model or the like, may be broadly classified as a positive mental state or a negative mental state by collapsing a profile of the user into a single dimensional score. For instance, the different categories of a POMS model may be given different weights, and the scores for the different categories may be weighted and summed to determine a composite score. The composite score may be ranked on a mental state scale, e.g., 0 to 28, 0 to 56, −28 to +28, etc. In one example, a threshold score may be used to segregate overall negative mental states/scores from overall positive mental states/scores. In one example, a hyperplane in a multidimensional space of moods/emotions may be used as a threshold to segregate overall positive mental states from overall negative mental states. In one example, the hyperplane/threshold may be determined based upon training data and test data (e.g., biometric data) for any one or more of users 171A-171D, and/or biometric data from other users, where the mental state may be known from direct observation by a medical professional, by self-reporting from the subject user(s), and so forth. It should be noted that in one example, the quantification of a user's mental state may include determining an actual mental state for the user. In another example, the user's mental state may be quantified as being an overall positive mental state, an overall negative mental state, or an overall neutral mental state, e.g., without actually determining a most likely mental state, such as: relaxed, content, cheerful, devastated, depressed, annoyed, indifferent, bored, etc. In still another example, the user's mental state may be quantified by scoring the user on a composite mental state scale.

In one example, the mental state coordinator 190 may be in communication with various devices through which automated actions to affect users' mental states may be implemented. For instance, mental state coordinator 190 may send instructions to lighting system 167 to cause lighting system 167 to dim the lights in a room in which user 171B is located. Similarly, mental state coordinator 190 may send instructions to coffee maker 169 to prepare a coffee for user 171A, e.g., with the intention that user 171A be presented with the coffee and in turn, to affect the mental state of user 171A. It should be noted that not all automated actions may have the same effect, or any measurable effect at all, with respect to different users. For instance, user 171A may find a warm coffee to be relaxing, while user 171B may never drink coffee and would simply be annoyed at having to waste a cup of coffee and to clean up. In another example, user 171B may be a child, and presenting the child with a cup of coffee would not be a reasonable automated action in any circumstance. Thus, in one example, any one or more of users 171A-171D may configure mental state coordinator 190 with rules as to which devices, e.g., smart appliances, PCs, mobile devices, etc. may be used to provide automated actions with respect any one or more of the 171A-171D, as well as which actions may be implemented via the respective devices. For instance, automated actions to affect the mental state of user 171A may include playing a video, presenting a picture, or playing a song via mobile device 170A, PC 166, TV 163A, etc. However, user 171B may be a child in the family and a parent (e.g., user 171A, 171C) may wish to minimize the child's daily media exposure. Thus, mental state coordinator 190 may be configured with a rule that no automated videos, pictures, or music may be played to affect the mood of the child, user 171B.

In one example, the present disclosure includes the selection and implementation of various automated actions in order to affect users' mental states in a predetermined manner. In one example, the predetermined manner may be an overall improvement of a mental state of a user. For instance, the present disclosure may seek to generate a measurable change in the mental state of a user from an overall negative mental state to an overall positive mental state. However, in one example, the present disclosure may seek to improve the mental state of a user, e.g., in a direction from negative towards positive. For instance, if a user has a composite mental state score of −25, an improvement of the composite score to −15 may be considered a positive improvement, despite the user still having an overall negative mental state/score.

As mentioned above, in one example, the present disclosure seeks to affect the mental states of two or more users in a predetermined manner. Thus, for example, if user 171A and user 171B are both determined to be in overall negative mental states, the present disclosure may seek to collectively improve the mental states/scores for users 171A and 171B. To illustrate, mental state coordinator 190 may determine that user 170A has a mental state score of −20, while user 171B has a mental state score of −15. In addition, mental state coordinator 190 may select to implement an automated action to affect the mental states of user 171A and 171B when the mental state coordinator 190 determines that users 171A and 171B are co-located, or that the users 171A and 171B are anticipated to be co-located at a later time, e.g., within a home associated with home network 160. In one example, the mental state coordinator 190 may determine that users 171A and 171B are co-located based upon Global Positioning System (GPS) location information which may be gathered by GPS units within mobile devices 170A and 170B and reported to mental state coordinator 190 via one or more networks. In one example, the mental state coordinator 190 may determine that users 171A and 171B are co-located based upon a local network discovery function whereby mental state coordinator 190 may determine that both mobile devices 170A and 170B are connected to home network 160.

Similarly, mental state coordinator 190 may determine the respective locations of users 171C and 171D based upon GPS location information gathered by and reported from mobile devices 170C and 170D. In another example, mental state coordinator 190 may determine the locations of user 171D based upon an Internet Protocol (IP address) of mobile device 170D. For instance, mobile device 170D may be connected to a wireless router in access network 140 and may be assigned an IP address that is local to access network 140. In still another example, mental state coordinator 190 may determine the location of user 171C based upon serving base station information, e.g., depending upon whether mobile device 170C is currently assigned to base station 152 or base station 153, and so forth. In one example, location information for various mobile devices may be gathered by one of application servers 114 in telecommunication network 110 and forwarded to mental state coordinator 190. In one example, anticipated locations of users and/or their mobile devices may be determined based upon current location information, trajectory information (e.g., if a mobile device is in motion), based upon time of day, day of week, etc., based upon historical location information of the users and/or their mobile devices, and so forth. For instance, if historical location information indicates that mobile device 170D is typically connected to access network 140 between the hours of 9:00 am and 6:00 pm on weekdays and that by 7:00 pm the mobile device 170D is typically connected to home network 160, the anticipated location of mobile device 170D, and user 171D, at 7:30 pm may be the location of home network 160. The current and/or anticipated locations of all of users 171A-171D and their mobile device 170A-170D may be determined in a same or a similar manner as outlined above.

In one example, the mental state coordinator 190 may have a number of available options for automated actions to affect the mental states of users 171A and 171B. For example, a number of automated actions may be implemented via mobile device 170A or 170B, TV 163A or TV 163B, PC 166, lighting system 167, thermostat 168, coffee maker 169, etc. The automated actions may include adjusting a temperature (up or down) via thermostat 168, presenting an audio program, a video program, an image, or a document for the first user and the second user via any capable device in home network 160 and/or one mobile devices 170A and 170B, preparing beverages for the first user and the second user, e.g., via coffee maker 169 or a similar device which may be capable of preparing teas, juices, sodas etc., adjusting a lighting level or a light pattern via lighting system 167, and so on.

In one example, the anticipated impact or effect of an automated action with respect to a user's mental state may be determined based upon an effectiveness score for the automated action with respect to the mental state of the user. For instance, as described above a user's mental state may be quantified as a mental state score. In addition, the mental state coordinator 190 may track the effectiveness of past implementations of various automated actions with respect to a particular user by comparing the mental state score of the user prior to the automated action to the mental state score of the user as determined after the implementation of the automated action. In one example, the effectiveness score may be based upon the magnitude of the change in the mental state score for the user. In addition, the effectiveness score may be aggregated and weighted over a number of past instances of the implementation of a same type of automated action for the user. Alternatively, or in addition, the effectiveness score may be aggregated and weighted over a number of past instances of the implementation of a same type of automated action for the user, and may further be segregated into scores for different times of day, or days of the week for which the automated action was implemented. In another example, an effectiveness score may be generated based upon a plurality of past instances where an automated action was implemented. However, the results of the users' mental state score changes may be weighted to favor more recent results as compared to results from further in the past, e.g., an exponentially weighted moving average, etc. In addition, results from prior to a certain time may be excluded, e.g., only results from within the previous six months, from within the previous year, etc. may be used to calculate the effectiveness score.

As an example, in a past instance, the application of an automated action of dimming the lights via lighting system 167 may have resulted in a change of mental state score for user 171A from −20 to −18. However, in a same or a different instance, an automated action of dimming the lights via lighting system 167 may have resulted in a change of mental state score for user 171B from −19 to −5. Thus, the effectiveness score for the automated action of light dimming may be greater for user 171B as compared to user 171A, e.g., an effectiveness score of 14 compared to an effectiveness score of 2. It should be noted that in one example, the effectiveness score may comprise a value representing the change in mental state score of a user. However, in another example, the effectiveness score may utilize a different scale and/or be weighted in a different manner where the effectiveness score does not directly correspond to the change in mental state score.

In one example, when selecting an automated action with respect to users 171A and 171B, the mental state coordinator 190 may select an automated action from among various available automated actions that the mental state coordinator 190 calculates will have a greatest anticipated impact (e.g., positively) with respect to the collective mental states of users 171A and 171B. For example, the mental state coordinator 190 may combine the effectiveness scores of an automated action with respect to both users 171A and 171B to determine a collective effectiveness score for the automated action. The mental state coordinator 190 may make similar calculations for different automated actions, and then select the automated action with the highest collective effectiveness score.

However, in one example, the selection of an automated action to affect the mental state of the first user and the mental state of the second user in the predetermined manner (e.g., positively), may be qualified by a priority ranking between the first user 171A and the second user 171B. For example, the automated action may be selected to have a greater anticipated effect on a mental state score of the first user 171A as compared to the mental state score of the second user 171B. For instance, even if an automated action is calculated to have a greatest collective effectiveness on the mental states of the first user 171A and the second user 171B, if the effectiveness score for the automated action for the first user 171A is less than that of second user 171B, the automated action may be omitted from consideration, or may be passed over by the mental state coordinator 190 in favor of a different automated action that will have a greater (positive) effect on the mental state of user 171A.

In one example, the priority ranking is based upon a relationship between the first user and the second user. For instance, user 171A may have a greater priority ranking than user 171B, where user 171A is a parent and user 171B is a child. To illustrate, the playing of a particular song may be determined to have a very high effectiveness score with respect to user 171B, the child. However, the parent, user 171A may dislike the song and the playing of the song may have an effectiveness score of zero (or even a slightly negative effectiveness score) with respect to user 171A. Thus, overall, the playing of the song may have a very high collective effectiveness score with respect to the combination of users 171A and 171B. Nevertheless, based upon the priority ranking of user 171A, the song will not be considered as a viable option for an automated action with respect to users 171A and 171B. Although the foregoing example illustrates where a parent may have a greater priority ranking than a child, in another example, a greater priority ranking may be assigned to a child, e.g., user 171B, as compared to a parent, e.g., user 171A. Other example relationships which may determine relative priority rankings may include a caregiver-charge relationship, a vendor-customer relationship, and so forth. In one example, the mental state coordinator 190 may provide a user-interface to enable users, e.g., users 171A-171D, to enter priority rankings, to authorize mental state coordinator 190 to interface with and provide instructions to networked devices via which automated actions may be implemented, and so forth. For instance, in one example, mental state coordinator 190 may function as a web-server and may provide a web-based user interface to PC 166, to one of mobile devices 170A-170D, etc., via which any one or more of the users 171A-171D may configure the mental state coordinator 190.

Continuing with the present example, upon selection of an automated action that is determined to have the greatest collective effectiveness with respect to the mental state scores of user 171A and 171B, the mental state coordinator 190 may then implement the automated action. For instance, implementing the automated action may comprise sending an instruction to a device in home network 160 to cause the resulting automated action, such as: adjusting a temperature (up or down) via thermostat 168, presenting an audio program, a video program, an image, or a document for the first user 171A and the second user 171B via any capable device in home network 160 and/or one mobile devices 170A and 170B, preparing beverages for the first user and the second user, e.g., via coffee maker 169 or a similar device which may be capable of preparing teas, juices, sodas etc., adjusting a lighting level or a light pattern via lighting system 167, and so on.

In one example, the mental state coordinator 190 may further track the actual effectiveness of the automated action with respect to the mental states of the first user 171A and the second user 171B. The tracking may include, for example, receiving updated biometric data for the first user 171A, re-quantifying mental state of first user 171A based upon the updated biometric data for the first user 171A, receiving updated biometric data for the second user 171B, and re-quantifying the mental state of the second user 171B based upon the updated biometric data for the second user 171B. In one example, it may be found that the mental state score for the first user 171A and/or the second user 171B was/were not affected to the extent predicted in accordance with the effectiveness score(s) for the automated action with respect to user 171A and/or user 171B. Thus, in one example, when the mental state coordinator 190 determines that the mental state of the first user 171A and the mental state of the second user 171B (individual and/or collectively) were not affected in the predetermined manner, e.g., as anticipated, the mental state coordinator 190 may select and implement a second automated action to affect the mental state of the first user 171A and the mental state of the second user 171B in a second predetermined manner. In one example, the mental state coordinator 190 may also decrease the effectiveness score of the first automated action for the first user 171A and/or decrease the effectiveness score of the first automated action for the second user 171B when it is determined that the mental state of the first user 171A and/or the mental state of the second user 171B (individually or collectively) were not affected in the first predetermined manner.

It should be noted that the foregoing example is described primarily in connection with an example where the mental state coordinator 190 is to increase (positively) the mental states of users 171A and 171B. However, in another example, the mental state coordinator 190 may attempt to maintain the mental states of users 171A and 171B. For instance, the mental state coordinator 190 may select and implement one or more automated actions so that the mental states of users 171A and 171B, collectively, do not become more negative. For instance, users 171A and 171B may both be in overall positive mental states (and may have corresponding mental state scores that are reflective of the overall positive mental states). Therefore, in one example, users 171A and 171B would like to remain in such overall positive mental states. However, in another example, the mental state coordinator 190 may actually select and implement one or more automated actions for the mental states of users 171A and 171B, collectively, to become more negative. For instance, users 171A and 171B may plan to watch a scary movie and may want to enhance certain mental states that are typically considered negative mental states, such as becoming more fearful, more apprehensive, etc., for entertainment purposes. Thus, the mental state coordinator 190 may actually select and implement one or more automated actions for the mental states of users 171A and 171B, collectively, to become more negative, such as making a room unpleasantly cold but turning off a heater or activating an air-conditioning via thermostat 168, by making a room very dark, via lighting system 167, by selecting certain songs to play, e.g., via speakers of PC 166, while users 171A and 171B may be eating dinner prior to watching the movie, and so forth. In this regard, it should be noted that any one or more of the functions of mental state coordinator 190 may be controlled and or adjusted by any one or more of the users 171A-171D who may be monitored by mental state coordinator 190 for purposes of affecting mental states, in accordance with the present disclosure. For example, the mental state coordinator 190 may never attempt to affect a user's mental state in a negative way unless a user provides explicit instructions to the mental state coordinator 190 to do so.

In addition, those skilled in the art will realize that the system 100 may be implemented in a different form than that which is illustrated in FIG. 1, or may be expanded by including additional endpoint devices, access networks, network elements, application servers, etc. without altering the scope of the present disclosure. For example, telecommunication network 110 is not limited to an IMS network, wireless access network 150 is not limited to a UMTS/UTRAN configuration, and so forth. Similarly, the present disclosure is not limited to an IP/MPLS network for VoIP telephony services, or any particular type of broadcast television network for providing television services. Various other configurations in accordance with the present disclosure are therefore possible. For instance, operations for affecting mental states of a first user and a second user may be implemented in PC 166 instead of having a separate mental state coordinator 190, the home network 160 may include additional network-connected devices, such as a stereo, wireless headphones, a humidistat, a fan, a window, curtains or blinds, a fireplace (e.g., an electric fireplace), an automated scent generator, and so forth. In another example, the access network 140 may include various additional devices via which automated actions to affect user's mental states may be implemented. In still another example, any functions described with respect to mental state coordinator 190 may be performed by application server 115 in telecommunication network 110. In such case, devices in home network 160 may be configured to accept instructions from application server 115, which resides outside home network 160. In one example, mental state coordinator 190 may receive instructions from application server 115, and may distribute such instructions to appropriate devices within the home network 160. In such an example, the operator of telecommunication network 110 may therefore provide a service for affecting users' mental states via the operator infrastructure in conjunction with devices deployed at one or more customer locations, such as home network 160. In this regard, it should be noted that automated actions may also be implemented with respect to devices deployed in various other networks. For instance, users 171A-171D may comprise a family with a vacation home having a different local area network from home network 160. In this case, automated actions may be implemented via both devices in home network 160 and devices located at the vacation home, depending upon where the users 171A-171D are presently located or anticipated to be located. Thus, these and other modifications are all contemplated within the scope of the present disclosure.

Figure 2:
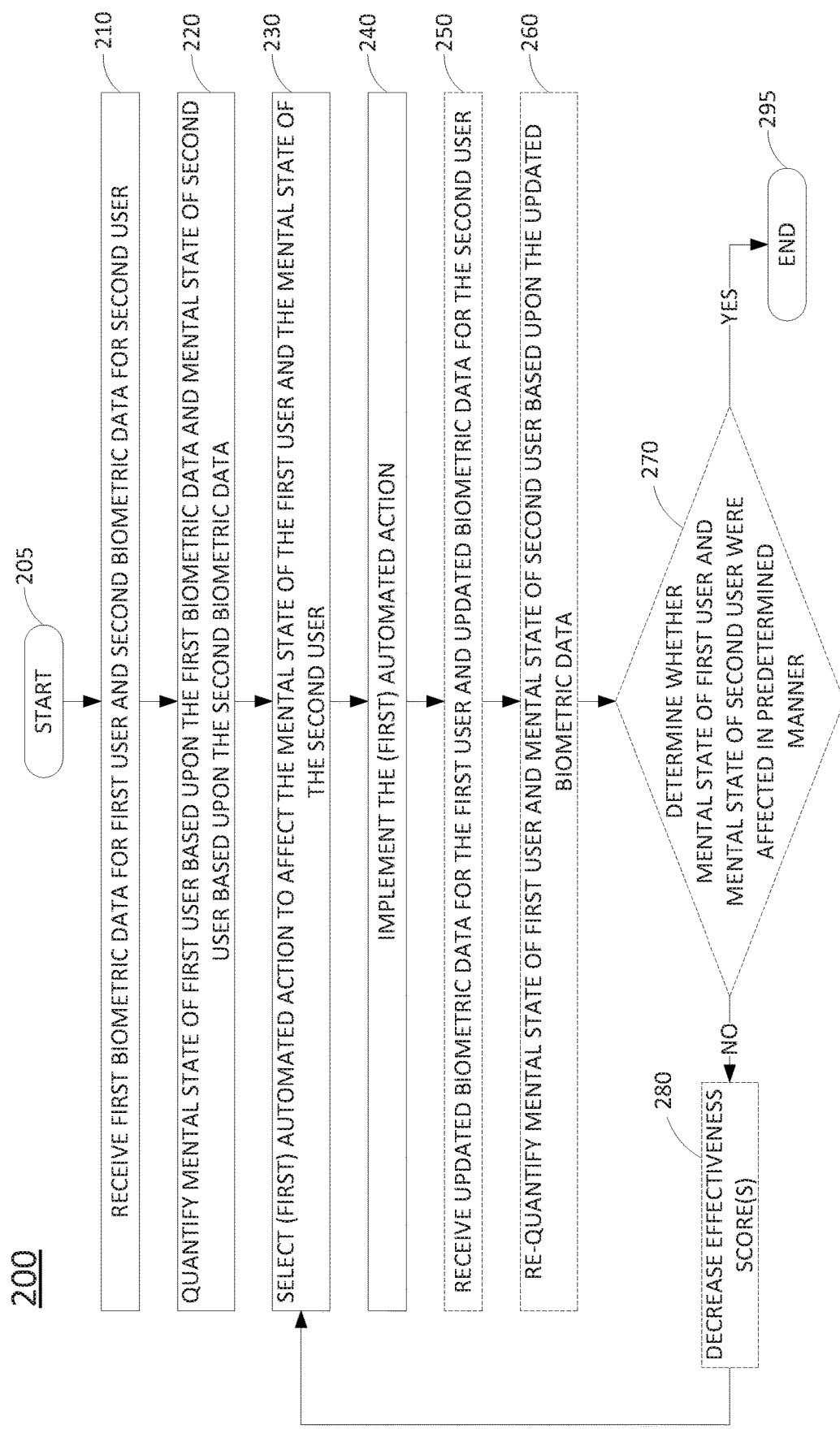
FIG. 2 illustrates a flowchart of an example method for affecting mental states of a first user and a second user.

FIG. 2 illustrates a flowchart of an example method 200 for affecting mental states of a first user and a second user, in accordance with the present disclosure. In one example, steps, functions and/or operations of the method 200 may be performed by a mental state coordinator. For example, the method 200 may be performed by mental state coordinator 190 in FIG. 1, or mental state coordinator 190 in conjunction with other components of home network 160 and system 100 in general. Similarly, the method 200 may be performed by application server 115 in FIG. 1, or application server 115 in conjunction with other components of the system 100, such as mobile devices 170A-170D and/or various devices within home network 160. In one example, the steps, functions, or operations of method 200 may be performed by a computing device or system 300, and/or processor 302 as described in connection with FIG. 3 below. For example, the system 300 may represent a mental state coordinator or an application server deployed in a telecommunication network, in accordance with the present disclosure. For illustrative purposes, the method 200 is described in greater detail below in connection with an example performed by a processor, such as processor 302. The method begins in step 205 and proceeds to step 210.

In step 210, the processor receives first biometric data for a first user and second biometric data for a second user. As mentioned above, users' biometric data may be gathered from various devices in a network, such as the users' mobile devices, via wearable devices/biometric sensors worn by the users, via personal computers, via smart TVs, and so forth. The first biometric data and the second biometric data may include various physical parameters of the first user and the second user, such as: facial image data, heart rates, breathing rates, skin conductance and/or sweat/skin moisture levels, temperature, voice pitch and tone, blood pressure, body movement information, postures, brain activity, e.g., electrical activity, optical activity, and/or chemical activity, and so forth.

In step 220, the processor quantifies a mental state of the first user based upon the first biometric data and quantifies a mental state of the second user based upon the second biometric data. For instance, different mental states may have different signatures or profiles to which the first biometric data and the second biometric data that is gathered and/or derived from various biometric sensors or other devices may be compared in order to determine a most likely current mental state for both of the first user and the second user. For instance, the processor may receive facial image data for the first user and facial image data for the second user, and may calculate the mental states of the first user and the second user, at least in part, using pattern matching, e.g., to eigenfaces representative of various mental states/moods. In another example, audio data of the first user and the second user may be compared to various signatures or profiles for different mental states that are based upon historical audio data for the first user, the second user, and/or other users. In one example, a mental state may be determined by comparing words and/or phrases in captured audio data to various profiles or signatures for different moods, e.g., where the profiles/signatures may comprise dictionaries or word lists that include words and/or phrases that are representative of the respective moods. In still another example, the mental states of the first user and the second user may be determined based, at least in part, upon heart rate or breathing rate data.

It should be noted that different types of biometric data may be aggregated and matched to signatures/patterns for different moods that are comprised of multiple data points that account for the different types of biometric data. Alternatively, or in addition, one or more types of biometric data may be used to match a pattern/signature for a mental state, while one or more other types of biometric data available for the user may be used to verify the accuracy of the mental state that is determined for the user. In addition, it should be noted that different types of biometric data may be gathered and utilized by the processor with regard to the first user and the second user. For instance, the mental state of the first user may be determined based upon facial image data, while the mental state of the second user may be determined based upon audio data and heart rate data.

In one example, the processor may categorize a user as being in an overall positive mental state, an overall negative mental state, or an overall neutral mental state (e.g., quantifying the user's mental state) based upon the mental state that may be determined from profile/signature matching. For instance, if it is determined that a user is "dejected," the user may be quantified as having an overall negative mental state. If it is determined that the user is "excited," the user may be quantified as having an overall positive mental state. Other examples of positive, negative, and neutral mental states are mentioned above. In one example, a user's mental state may be broadly classified as being a positive mental state or a negative mental state by quantifying the mental state/mood within a two or three dimensional space, e.g., according to an evaluative space model, a circumplex model, a vector model, a PANA model, or the like. In one example, a user's mental state/mood may be categorized along one or more scales or dimensions, e.g., a Profile of Mood States (POMS) or the like. In one example, a user's mental state/mood that is quantified along one or more scales or dimensions, e.g., in a profile in accordance with POMS, PANA, a circumplex model, a vector model or the like, may be broadly classified as a positive mental state, a negative mental state, or a neutral mental state by collapsing the profile of the user into a single dimensional score. For instance, the different categories of a POMS model may be given different weights, and the scores for the different categories may be weighted and summed accordingly, to determine a composite score. In one example, a threshold score may be used to segregate overall negative mental states/scores from overall positive mental states/scores. In one example, two thresholds may be deployed to segregate overall positive, neutral, and negative mental state scores. In one example, a hyperplane in a multidimensional space of moods/emotions may be used as a threshold to segregate overall positive mental states from overall negative mental states. In one example, mental states that are within a threshold distance of the hyperplane may be considered neutral mental state scores.

In step 230, the processor selects an automated action to affect the mental state of the first user and the mental state of the second user. In one example, the processor selects the first automated action from among a plurality of available automated actions in accordance with an effectiveness score of the first automated action for the first user and an effectiveness score of the first automated action for the second user. In one example, the automated action comprises a first automated action to affect the mental state of the first user and the mental state of the second user in a predetermined manner (e.g., a first predetermined manner). In one example, the predetermined manner is to increase at least one of the first mental state score or the second mental state score. In another example, the predetermined manner is to maintain, at a same level, at least one of the first mental state score or the second mental state score. In still another example, the predetermined manner is to decrease at least one of the first mental state score or the second mental state score (with the consents/authorizations of the first user and the second user, e.g., for entertainment purposes).

In one example, the (first) automated action is selected to affect the mental state of the first user and the mental state of the second user in a (first) predetermined manner based upon a priority ranking between the first user and the second user. For instance, the automated action may be selected to have a greater anticipated effect on the first mental state score as compared to the second mental state score, in accordance with the first predetermined manner. In one example, the priority ranking is based upon a relationship between the first user and the second user, such as: a parent-child relationship, a caregiver-charge relationship, a vendor-client relationship, and so forth.

In one example, the first automated action is selected at step 230 for implementation at a location where the first user and the second user are anticipated to be co-located (e.g., if the users are co-located and are anticipated to remain co-located, or if the users are at different locations, but are anticipated to be co-located at a later time). Thus, for example, the plurality of automated actions from which the automated action is selected may include automated actions that can be implemented on the devices that are available at such location. In various examples, the first automated action may comprise: adjusting a temperature (up or down) of an environment associated with the first user and the second user (e.g., at a location where the first user and second user are co-located and/or will be co-located); presenting an audio program, a video program, an image, or a document for the first user and the second user; adjusting a lighting of the environment associated with the first user and the second user; preparing beverages for the first user and the second user; and so on.

In step 240, the processor implements the (first) automated action to affect the mental state of the first user and the mental state of the second user. In one example, the automated action is implemented at the location where the first user and the second user are anticipated to be co-located. For instance, the automated action may be implemented via at least one of an appliance at the location, or via a mobile device of the first user or the second user (which may also be at the location). For instance, the processor may send an instruction to a lighting system to cause lighting system to dim the lights in a room in which the first user and the second user are located, or are anticipated to be located together, the processor may send an instruction to a coffee maker to prepare (at least) two cups of coffee for the first user and the second user, the processor may send an instruction to a TV or set-top box to play a particular video program, the processor may send an instruction to a stereo system to play a particular audio program, and so forth.

In optional step 250, the processor may receive updated biometric data for the first user and updated biometric data for the second user. For instance, during and/or following the implementation of the automated action, the processor may continue to receive biometric data for the first and the second user from the same or a different set of source devices as noted above in connection with step 210.

In optional step 260, the processor may re-quantify the mental state of the first user based upon the updated biometric data for the first user and re-quantify the mental state of the second user based upon the updated biometric data for the second user. For instance, optional step 260 may comprise the same or similar operations as described above in connection with step 220, e.g., with respect to the updated biometric data for the first user and the updated biometric data for the second user. To illustrate, the processor may generate an updated mental state score for the first user and an updated mental state score for the second user based upon the updated biometric data for the first user and the second user, respectively. Alternatively, or in addition, the processor may more broadly re-quantify the mental state of the first user as being either overall positive, neutral, or negative, and similarly for the mental state of the second user.

In optional step 270, the processor may determine whether the mental state of the first user and the mental state of the second user were affected in the first predetermined manner. For instance, the processor may compare a mental state score for the first user after the implementation of the automated action to the mental state score for the first user prior to the implementation of the automated action. If the predetermined manner was to increase the mental state scores for the first user and the second user, a change in mental state score of either or both users to be more positive and/or to increase, may be considered a result where the mental state scores were affected in the predetermined manner. However, if either or both of the mental state scores decline/become more negative, this may be considered a result where the mental state scores were not affected in the predetermined manner. In one example, optional step 270 may collectively consider the change (or lack thereof) in mental states scores for both the first user and the second user. For example, if the predetermined manner was to increase, collectively, the mental state scores of the first user and the second user, and if the mental state score of the second user declined slightly, but the mental state score of the first user increased significantly (e.g., a change of greater magnitude in the positive direction as compared to the negative decline of the mental state score of the second user), this may be considered a result where the mental state scores were affected in the predetermined manner.

In one example, the change in mental state may be measured in terms of directionality, e.g., without quantification of magnitude. For instance, the change in mental state may be from overall negative to neutral or overall positive. In another example, a lack of change in the mental state may comprise a user remaining in a neutral mental state. This may be the case even where a mental state that is determined for a user after the implementation of the automated action may be a different mental state than a mental state of the user prior to the implementation of the automated action. For instance, the user's mental state may change from "indifferent" to "bored," but the quantification of the mental state may remain as "neutral," e.g., 0 on a scale of −1 to +1. When the processor determines that the mental state of the first user and the mental state of the second user were affected in the first predetermined manner, the method 200 may proceed to step 295 where the method ends. Otherwise, when the processor determines that the mental state of the first user and the mental state of the second user were not affected in the first predetermined manner, the method 200 may proceed to optional step 280.

In optional step 280, the processor may decrease an effectiveness score of the first automated action for the first user and/or decrease an effectiveness score of the first automated action for the second user. For instance, where the mental state score of either the first user or the second user did not change in an intended direction in accordance with the (first) predetermined action, the effectiveness score of the automated action with respect to the first user and/or the effectiveness score of the automated action with respect to the second user may be reduced. For example, as described above, the effectiveness scores for various automated actions with respect to a user may be determined based upon quantifications of a mental state of the user before and after an implementation of an automated action, e.g., over one or more historical occasions where the automated action was implemented. Thus, the results of the implementation of the automated action at step 240 may be added as additional historic data from which the effectiveness score is determined.

Following optional step 280, the method 200 may return to step 230. For instance, in repeating step 230 the processor may select a second automated action to affect the mental state of the first user and the mental state of the second user, e.g., in a second predetermined manner. In repeating step 240, the processor may implement the second automated action. Following the repeat of step 240, the method 200 may proceed to step 295 where the method ends, or may again proceed to optional step 250 to receive updated biometric data for the first user and update biometric data for the second user, to re-quantify the mental states of the first user and the second user at optional step 260, to determine whether the mental state of the first user and the mental state of the second user were affected in the second predetermined manner at optional step 270, and so forth. Following a second iteration of optional step 270, the method 200 either proceeds again to optional step 280 and returns to step 230, or proceeds to step 295 where the method 200 ends. It should be noted that in one example, step 230 may be returned to on an ongoing basis, e.g., as long as the processor is deployed for performing steps, functions, and/or operations in connection with the method 200 for affecting mental states of a first user and a second user.

It should be noted that the method 200 may be expanded to include additional steps, or to include modifications or additions to the steps recited. For example, the method 200 may be expanded to perform operations to affect the mental state(s) of a third user, a fourth user, etc., in addition to the mental states of the first user and the second user. In another example, steps 230 and 240 may be expanded to comprise selecting and deploying a plurality of automated actions at the same time. For instance, two automated actions that are anticipated to have a similar effect on the users' mental states (e.g., to both affect the users' mental states positively), may be selected an implemented together, such as turning on a movie that is liked by both the first user and the second user, and preparing two cups of coffee which both users enjoy drinking. Thus, these and other modifications are all contemplated within the scope of the present disclosure.

In addition, although not specifically specified, one or more steps, functions or operations of the method 200 may include a storing, displaying and/or outputting step as required for a particular application. In other words, any data, records, fields, and/or intermediate results discussed in the method 200 can be stored, displayed and/or outputted either on the device executing the method 200, or to another device, as required for a particular application. Furthermore, steps, blocks, functions, or operations in FIG. 2 that recite a determining operation or involve a decision do not necessarily require that both branches of the determining operation be practiced. In other words, one of the branches of the determining operation can be deemed as an optional step. In addition, one or more steps, blocks, functions, or operations of the above described method 200 may comprise optional steps, or can be combined, separated, and/or performed in a different order from that described above, without departing from the examples of the present disclosure.

As such, the present disclosure provides at least one advancement in the technical fields of telecommunication service provider network operations, home network or other local area network operations, and the use of network-connected appliances. In particular, network-connected appliances enable various efficiencies, such as remotely adjusting a home thermostat from a different location, remotely programming DVR devices, and so forth. However, in accordance with the present disclosure, various network-connected appliances may be configured to quantitatively improve the mental states of various users (or otherwise affect the metal states in a predetermined manner). In addition, addressing mental health issues has typically been a qualitative endeavor. On the other hand, in accordance with the present disclosure measurable biometric data is gathered from various biometric sensors or other network-connected devices, and users' mental states may be determined and/or quantified based upon the biometric data, e.g., as opposed to responding to survey questions, having a discussion with a medical professional who may categorizes the user's mental state based upon his/her personal expertise, and so forth. In this regard, the present disclosure also provides a transformation of data, e.g., biometric data is generated by biometric sensors and/or network-connected devices and is transformed into mental state scores, profiles, or other quantification of mental state that may then be used to select automated actions which may affect the users' mental states in a predetermined manner. In addition, the data quantifying users' mental states is also transformed into additional data or new data that comprising effectiveness scores for various automated actions which may affect the users' mental states in various predetermined manners, e.g., positively, negatively, etc. Finally, examples of the present disclosure improve the functioning of a computing device, e.g., a server. Namely, a server deployed in a telecommunication service provider network, or in a home network or other local network is improved by the use of biometric data to quantify users' mental states and to select automated actions to affect the users' mental states in predetermined manners.

Figure 3:
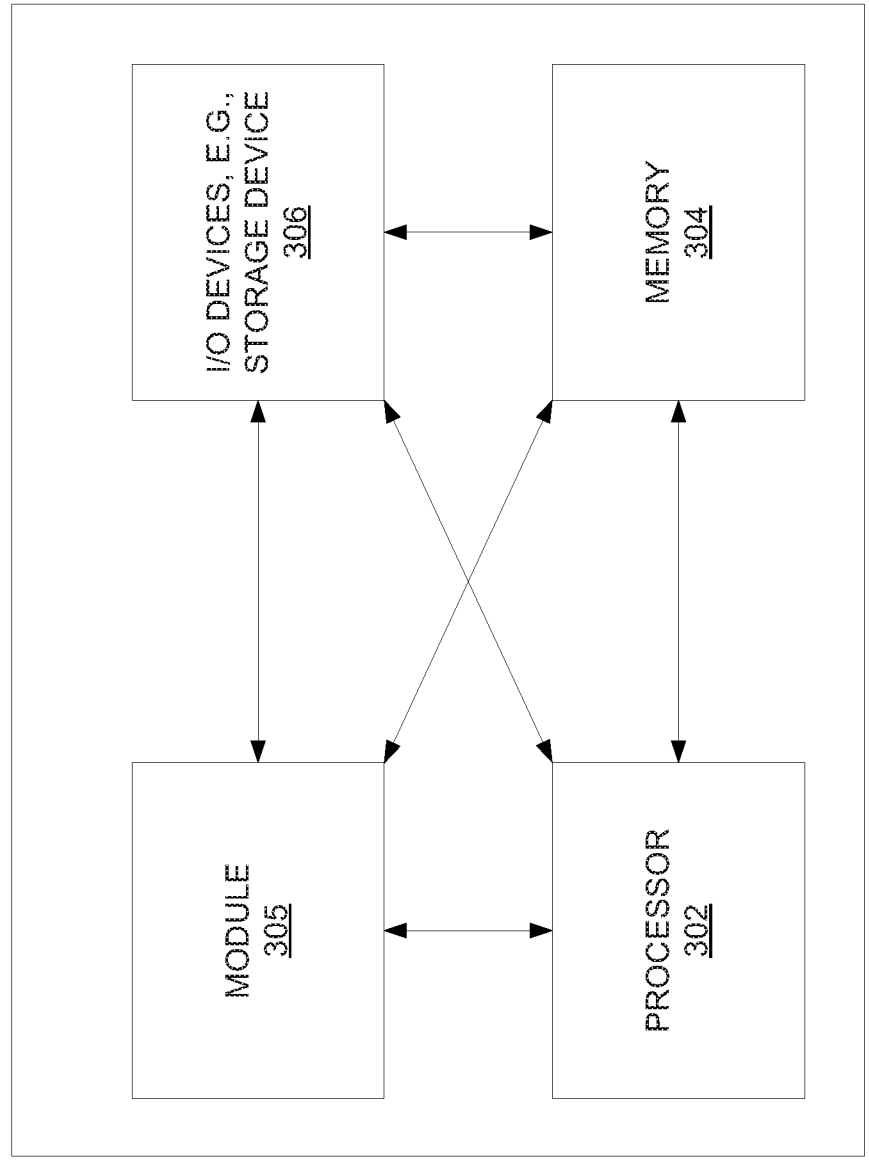
FIG. 3 illustrates an example high-level block diagram of a computer specifically programmed to perform the steps, functions, blocks, and/or operations described herein.

FIG. 3 depicts a high-level block diagram of a computing device specifically programmed to perform the functions described herein. As depicted in FIG. 3, the system 300 comprises one or more hardware processor elements 302 (e.g., a central processing unit (CPU), a microprocessor, or a multi-core processor), a memory 304 (e.g., random access memory (RAM) and/or read only memory (ROM)), a module 305 for affecting mental states of a first user and a second user, and various input/output devices 306 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). Although only one processor element is shown, it should be noted that the computing device may employ a plurality of processor elements. Furthermore, although only one computing device is shown in the figure, if the method 200 as discussed above is implemented in a distributed or parallel manner for a particular illustrative example, i.e., the steps of the method, or the entire method is implemented across multiple or parallel computing devices, then the computing device of this figure is intended to represent each of those multiple computing devices.

Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented. The one or more hardware processors 302 can also be configured or programmed to cause other devices to perform one or more operations as discussed above. In other words, the one or more hardware processors 302 may serve the function of a central controller directing other devices to perform the one or more operations as discussed above.

It should be noted that the present disclosure can be implemented in software and/or in a combination of software and hardware, e.g., using application specific integrated circuits (ASIC), a programmable gate array (PGA) including a Field PGA, or a state machine deployed on a hardware device, a computing device or any other hardware equivalents, e.g., computer readable instructions pertaining to the method discussed above can be used to configure a hardware processor to perform the steps, functions and/or operations of the above disclosed method. In one example, instructions and data for the present module or process 305 for affecting mental states of a first user and a second user (e.g., a software program comprising computer-executable instructions) can be loaded into memory 304 and executed by hardware processor element 302 to implement the steps, functions or operations as discussed above in connection with the illustrative method 200. Furthermore, when a hardware processor executes instructions to perform "operations," this could include the hardware processor performing the operations directly and/or facilitating, directing, or cooperating with another hardware device or component (e.g., a co-processor and the like) to perform the operations.

The processor executing the computer readable or software instructions relating to the above described method can be perceived as a programmed processor or a specialized processor. As such, the present module 305 for affecting mental states of a first user and a second user (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. Furthermore, a "tangible" computer-readable storage device or medium comprises a physical device, a hardware device, or a device that is discernible by the touch. More specifically, the computer-readable storage device may comprise any physical devices that provide the ability to store information such as data and/or instructions to be accessed by a processor or a computing device such as a computer or an application server.

While various examples have been described above, it should be understood that they have been presented by way of illustration only, and not a limitation. Thus, the breadth and scope of any aspect of the present disclosure should not be limited by any of the above-described examples, but should be defined only in accordance with the following claims and their equivalents.

What is claimed is:

1. A device comprising:
    a processor; and
    a computer-readable medium storing instructions which, when executed by the processor when deployed in a communication network, cause the processor to perform operations, the operations comprising:
        receiving first biometric data for a first user, wherein the first biometric data comprises first facial image data of the first user from a first mobile device in communication with the processor;
        quantifying a mental state of the first user based upon the first biometric data, wherein the quantifying the mental state of the first user includes pattern matching the first facial image data to a first eigenface from among a plurality of eigenfaces representing a plurality of different mental states, wherein the first eigenface represents the mental state of the first user;
        receiving second biometric data for a second user, wherein the second biometric data comprises second facial image data of the second user from a second mobile device in communication with the processor;
        quantifying a mental state of the second user based upon the second biometric data, wherein the quantifying the mental state of the second user includes pattern matching the second facial image data to a second eigenface from among the plurality of eigenfaces, wherein the second eigenface represents the mental state of the second user;
        selecting a first automated action to affect the mental state of the first user and the mental state of the second user; and
        implementing the first automated action to affect the mental state of the first user and the mental state of the second user, wherein the first automated action is implemented via an instruction to an apparatus at a location where the first user and the second user are anticipated to be co-located.

2. The device of claim 1, wherein the operations further comprise:
    receiving updated biometric data for the first user;
    re-quantifying the mental state of the first user based upon the updated biometric data for the first user;
    receiving updated biometric data for the second user; and
    re-quantifying the mental state of the second used based upon the updated biometric data for the second user.

3. The device of claim 2, wherein the first automated action is selected to affect the mental state of the first user and the mental state of the second user in a first predetermined manner.

4. The device of claim 3, wherein the operations further comprise:
    determining that the mental state of the first user and the mental state of the second user were not affected in the first predetermined manner;
    selecting a second automated action to affect the mental state of the first user and the mental state of the second user in a second predetermined manner; and
    implementing the second automated action to affect the mental state of the first user and the mental state of the second user in the second predetermined manner.

5. The device of claim 4, wherein the first automated action is selected from among a plurality of available automated actions in accordance with an effectiveness score of the first automated action for the first user and an effectiveness score of the first automated action for the second user, wherein each of the plurality of available automated actions is assigned an effectiveness score for the first user and an effectiveness score for the second user.

6. The device of claim 5, wherein each effectiveness score is based upon quantifications of a mental state of a respective user before and after an implementation of an automated action.

7. The device of claim 5, wherein, when it is determined that the mental state of the first user and the mental state of the second user were not affected in the first predetermined manner, the operations further comprise at least one of:
    decreasing the effectiveness score of the first automated action for the first user; or
    decreasing the effectiveness score of the first automated action for the second user.

8. The device of claim 1, wherein the mental state of the first user is quantified into a first mental state score based upon the first biometric data, and wherein the mental state of the second user is quantified into a second mental state score based upon the second biometric data.

9. The device of claim 8, wherein the first automated action is selected to affect the mental state of the first user and the mental state of the second user in a first predetermined manner.

10. The device of claim 9, wherein the first predetermined manner is to increase at least one of: the first mental state score or the second mental state score.

11. The device of claim 9, wherein the first predetermined manner is to decrease at least one of: the first mental state score or the second mental state score.

12. The device of claim 9, wherein the first predetermined manner is to maintain at least one of: the first mental state score or the second mental state score.

13. The device of claim 9, wherein the first automated action is selected to affect the mental state of the first user and the mental state of the second user in the first predetermined manner based upon a priority ranking between the first user and the second user.

14. The device of claim 13, wherein the first automated action is selected to have a greater anticipated effect on the first mental state score as compared to the second mental state score, in accordance with the first predetermined manner.

15. The device of claim 14, wherein the priority ranking is based upon a relationship between the first user and the second user, wherein the relationship comprises one of:
a parent-child relationship;
a caregiver-charge relationship; or
a vendor-client relationship.

16. The device of claim 1, wherein the first automated action comprises:
adjusting a temperature of an environment associated with the first user and the second user;
presenting an audio program, a video program, an image, or a document for the first user and the second user;
adjusting a lighting of the environment associated with the first user and the second user; or
preparing beverages for the first user and the second user.

17. The device of claim 1, wherein the apparatus comprises at least one of:
an appliance at the location;
a television at the location;
a stereo at the location;
the first mobile device; or
the second mobile device.

18. A non-transitory computer-readable medium storing instructions which, when executed by a processor deployed in a communication network, cause the processor to perform operations, the operations comprising:
receiving first biometric data for a first user, wherein the first biometric data comprises first facial image data of the first user from a first mobile device in communication with the processor;
quantifying a mental state of the first user based upon the first biometric data, wherein the quantifying the mental state of the first user includes pattern matching the first facial image data to a first eigenface from among a plurality of eigenfaces representing a plurality of different mental states, wherein the first eigenface represents the mental state of the first user;
receiving second biometric data for a second user, wherein the second biometric data comprises second facial image data of the second user from a second mobile device in communication with the processor;
quantifying a mental state of the second user based upon the second biometric data, wherein the quantifying the mental state of the second user includes pattern matching the second facial image data to a second eigenface from among the plurality of eigenfaces, wherein the second eigenface represents the mental state of the second user;
selecting a first automated action to affect the mental state of the first user and the mental state of the second user; and
implementing the first automated action to affect the mental state of the first user and the mental state of the second user, wherein the first automated action is implemented via an instruction to an apparatus at a location where the first user and the second user are anticipated to be co-located.

19. A method, comprising:
receiving, by a processor deployed in a communication network, first biometric data for a first user, wherein the first biometric data comprises first facial image data of the first user from a first mobile device in communication with the processor;
quantifying, by the processor, a mental state of the first user based upon the first biometric data, wherein the quantifying the mental state of the first user includes pattern matching the first facial image data to a first eigenface from among a plurality of eigenfaces representing a plurality of different mental states, wherein the first eigenface represents the mental state of the first user;
receiving, by the processor, second biometric data for a second user, wherein the second biometric data comprises second facial image data of the second user from a second mobile device in communication with the processor;
quantifying, by the processor, a mental state of the second user based upon the second biometric data, wherein the quantifying the mental state of the second user includes pattern matching the second facial image data to a second eigenface from among the plurality of eigenfaces, wherein the second eigenface represents the mental state of the second user;
selecting, by the processor, a first automated action to affect the mental state of the first user and the mental state of the second user; and
implementing, by the processor, the first automated action to affect the mental state of the first user and the mental state of the second user, wherein the first automated action is implemented via an instruction to an apparatus at a location where the first user and the second user are anticipated to be co-located.

* * * * *